(12) United States Patent
Bratescu et al.

(10) Patent No.: US 9,220,669 B2
(45) Date of Patent: Dec. 29, 2015

(54) RESVERATROL FERULATE COMPOUNDS, COMPOSITIONS CONTAINING THE COMPOUNDS, AND METHODS OF USING THE SAME

(75) Inventors: Daniela Bratescu, Northport, NY (US); Faterneh Mohammadi, Hauppauge, NY (US); Julius R. Zecchino, New York, NY (US); Fred Daneshyar, Smithtown, NY (US)

(73) Assignee: ELC Management LLC, New York, NY (US)

( * ) Notice: Subject to any disclaimer, the term of this patent is extended or adjusted under 35 U.S.C. 154(b) by 415 days.

(21) Appl. No.: 12/775,676

(22) Filed: May 7, 2010

(65) Prior Publication Data

US 2010/0215755 A1    Aug. 26, 2010

Related U.S. Application Data

(62) Division of application No. 12/204,064, filed on Sep. 4, 2008, now abandoned.

(60) Provisional application No. 60/970,943, filed on Sep. 8, 2007, provisional application No. 61/029,600, filed on Feb. 19, 2008.

(51) Int. Cl.
*A61K 31/235* (2006.01)
*A61K 8/37* (2006.01)
*A61Q 19/02* (2006.01)
*A61Q 19/08* (2006.01)
*A61Q 1/02* (2006.01)

(52) U.S. Cl.
CPC ............... *A61K 8/375* (2013.01); *A61Q 19/02* (2013.01); *A61Q 19/08* (2013.01); *A61K 2800/31* (2013.01); *A61K 2800/522* (2013.01); *A61Q 1/02* (2013.01)

(58) Field of Classification Search
USPC .................................. 424/62; 514/532, 533
See application file for complete search history.

(56) References Cited

U.S. PATENT DOCUMENTS

| | | |
|---|---|---|
| 3,215,724 A | 11/1965 | Strobel et al. |
| 3,439,088 A | 4/1969 | Edman |
| 3,781,417 A | 12/1973 | Weiters et al. |
| 3,818,105 A | 6/1974 | Coopersmith et al. |
| 4,003,966 A | 1/1977 | Napier et al. |
| 4,677,152 A | 6/1987 | Allen et al. |
| 4,702,844 A | 10/1987 | Flesher et al. |
| 4,803,067 A | 2/1989 | Brunetta et al. |
| 4,970,252 A | 11/1990 | Sakuta et al. |
| 5,118,496 A | 6/1992 | Herstein |
| 5,183,588 A | 2/1993 | Salerno et al. |
| 5,183,589 A | 2/1993 | Brunetta et al. |
| 5,236,986 A | 8/1993 | Sakuta |
| 5,412,004 A | 5/1995 | Tachibana et al. |
| 5,549,281 A | 8/1996 | Hall |
| 5,654,362 A | 8/1997 | Schulz, Jr. et al. |
| 5,736,161 A | 4/1998 | Garces et al. |
| 5,760,116 A | 6/1998 | Kilgour et al. |
| 5,808,119 A | 9/1998 | Nkiliza |
| 5,811,487 A | 9/1998 | Schulz, Jr. et al. |
| 5,824,326 A | 10/1998 | Crotty et al. |
| 5,837,793 A | 11/1998 | Harashima et al. |
| 5,843,193 A | 12/1998 | Hawkins et al. |
| 5,916,543 A | 6/1999 | Kaplan |
| 6,147,121 A | 11/2000 | Breton et al. |
| 6,270,780 B1 | 8/2001 | Carson et al. |
| 6,358,517 B1 | 3/2002 | Pillai et al. |
| 6,407,142 B1 | 6/2002 | Courbriere et al. |
| 6,440,433 B1 | 8/2002 | Breton et al. |
| 6,465,402 B1 | 10/2002 | Lorant |
| 6,497,861 B1 | 12/2002 | Wang et al. |
| 6,524,595 B1 | 2/2003 | Perrier et al. |
| 6,531,132 B1 | 3/2003 | Paufique |
| 6,572,882 B1 | 6/2003 | Vercauteren et al. |
| 6,573,299 B1 | 6/2003 | Petrus |
| 6,610,322 B1 | 8/2003 | Keller et al. |
| 6,872,401 B2 | 3/2005 | Seyler et al. |
| 6,958,160 B1 | 10/2005 | Keller et al. |
| 6,969,531 B2 | 11/2005 | Dehazya et al. |
| 6,979,440 B2 | 12/2005 | Shefer et al. |
| 7,026,518 B2 | 4/2006 | Gokaraju et al. |
| 7,115,282 B2 | 10/2006 | Shefer et al. |
| 7,150,883 B2 | 12/2006 | Keller et al. |
| 7,714,161 B2 | 5/2010 | Andrus et al. |
| 8,048,456 B2 * | 11/2011 | Burke-Colvin et al. ...... 424/725 |
| 2002/0022040 A1 | 2/2002 | Robinson et al. |
| 2002/0051799 A1 | 5/2002 | Pruche et al. |
| 2002/0183400 A1 | 12/2002 | Baldo et al. |

(Continued)

FOREIGN PATENT DOCUMENTS

| | | |
|---|---|---|
| DE | 19638534 | 3/1998 |
| EP | 0945425 | 9/1999 |

(Continued)

OTHER PUBLICATIONS

The American Heritage Dictionary of the English Language, 1 page. (Admitted Prior Art).
http://www.gnpd.com; Mintel; Megadose; Record ID: 519633; Klinger Advanced Aesthetics; Cosmedicine; Skincare; Face/Neck Care; USA; Apr. 2006.
http://www.gnpd.com; Mintel; Mushroom Face Serum; Record ID: 425030; Origins Natural Resources; Dr. Andrew Weil for Origins Plantidote; Skincare; Face/Neck Care; USA; Jan. 2006.
http://gnpd.com; Mintel; All Brightening Serum Special Set; Record ID: 325773; Enprani; Enprani Lastian; Skincare; Face/Neck Care; South Korea; Dec. 2004.

(Continued)

*Primary Examiner* — Rei-Tsang Shiao
(74) *Attorney, Agent, or Firm* — Julie Blackburn

(57) ABSTRACT

The present invention relates to methods of using topical or cosmetic compositions containing resveratrol ferulates for skin lightening and anti-aging applications and method of synthesizing resveratrol ferulates.

9 Claims, 5 Drawing Sheets

(56) References Cited

U.S. PATENT DOCUMENTS

| | | |
|---|---|---|
| 2002/0197228 A1 | 12/2002 | LaSala et al. |
| 2003/0124161 A1 | 7/2003 | Biatry et al. |
| 2003/0190337 A1 | 10/2003 | Bissett |
| 2004/0009197 A1 | 1/2004 | DeRosa et al. |
| 2004/0071639 A1 | 4/2004 | Perricone |
| 2004/0109894 A1 | 6/2004 | Shefer et al. |
| 2004/0121019 A1 | 6/2004 | Perrier et al. |
| 2004/0126337 A1 | 7/2004 | Singleton |
| 2004/0209951 A1 | 10/2004 | Gokaraju et al. |
| 2004/0254357 A1 | 12/2004 | Zaloga et al. |
| 2005/0048008 A1 | 3/2005 | Gupta |
| 2005/0106196 A1 | 5/2005 | Cassin et al. |
| 2005/0118218 A1 | 6/2005 | Cassin |
| 2005/0142079 A1 | 6/2005 | Garrison et al. |
| 2005/0147631 A1 | 7/2005 | Goldstein et al. |
| 2005/0220733 A1 | 10/2005 | Tsuzuki et al. |
| 2006/0002884 A1 | 1/2006 | Golz-Berner et al. |
| 2006/0018869 A1 | 1/2006 | Stab et al. |
| 2006/0210513 A1 | 9/2006 | Luizzi et al. |
| 2007/0009455 A1 | 1/2007 | Kim et al. |
| 2007/0015840 A1 | 1/2007 | Dalko et al. |
| 2007/0110731 A1 | 5/2007 | Riley |
| 2007/0160550 A1 | 7/2007 | Charles nee Newsham et al. |
| 2007/0166269 A1 | 7/2007 | Cassin et al. |
| 2008/0044373 A1 | 2/2008 | Ilekti et al. |
| 2008/0076833 A1 | 3/2008 | Van Brussel et al. |
| 2008/0095866 A1 | 4/2008 | DeClercq et al. |
| 2008/0138393 A1 | 6/2008 | Leverett et al. |
| 2009/0035236 A1 | 2/2009 | Maes et al. |
| 2009/0035237 A1 | 2/2009 | Maes et al. |
| 2009/0035240 A1 | 2/2009 | Maes et al. |
| 2009/0035242 A1 | 2/2009 | Maes et al. |
| 2009/0035243 A1 | 2/2009 | Czarnota et al. |
| 2009/0047309 A1* | 2/2009 | Maes et al. ............ 424/401 |
| 2009/0068132 A1 | 3/2009 | Bratescu et al. |
| 2009/0215881 A1 | 8/2009 | Delaire et al. |
| 2010/0216879 A1* | 8/2010 | Maes et al. ............ 514/533 |
| 2012/0288460 A1 | 11/2012 | Maes et al. |
| 2012/0288461 A1 | 11/2012 | Maes et al. |

FOREIGN PATENT DOCUMENTS

| | | |
|---|---|---|
| EP | 0 980 235 | 5/2003 |
| EP | 1634576 | 3/2006 |
| EP | 1640041 | 3/2006 |
| FR | 2862533 | 5/2005 |
| FR | 2867977 | 9/2005 |
| JP | 61-018708 | 1/1986 |
| JP | 2002-080372 | 3/2002 |
| JP | 2004-532790 | 10/2004 |
| WO | WO99/04747 | 2/1999 |
| WO | WO 01/030336 | 5/2001 |
| WO | WO 01/91695 | 12/2001 |
| WO | WO-01/97769 | 12/2001 |
| WO | WO2004/000302 | 12/2003 |
| WO | WO2004/024798 | 3/2004 |
| WO | WO-2004/054533 | 7/2004 |
| WO | WO2005/069998 | 8/2005 |
| WO | WO2006/029484 | 3/2006 |
| WO | WO2006029483 | 3/2006 |
| WO | WO2006078941 | 7/2006 |
| WO | WO2006/134282 | 12/2006 |

OTHER PUBLICATIONS http://www.gnpd.com; Mintel; Advanced-C Eye Toning Gel; Record ID: 10179173: Cellex-C International; Cellex-C; Skincare; Facial/Neck Care; USA; Aug. 2004.

http://www.gnpd.com; Mintel; Pressed Powder; Record ID: 10178742; Aveda; Aveda Inner Light; Colour Cosmetics; Face Colour Cosmetics—Powder; USA; Jul. 2004.

http://www.gnpd.com; Mintel; Lifting Serum; Record ID: 231615; Caudalie; Caudalie; Skincare; Face/Neck Care; France; Oct. 2003.

http://www.gnpd.com; Mintel; DayWear Plus Anti-Oxidant Crème SPF 15; Record ID: 201446; Estee Lauder; Estee Lauder; Colour Cosmetics; Skincare; Sun-Sun/Sunbed Exposure; UK; Apr. 2003.

http://www.gnpd.com; Mintel; Multi-Protection Anti-Oxidant Moisturizer SPF 15; Record ID: 10126373; Estee Lauder; Estee Lauder DayWear Plus; Skincare; Face/Neck Care; USA; Jan. 2003.

http://www.gnpd.com; Mintel; Eye Lifting Serum; Record ID: 10174853; Caudalie; Caudalie; Skincare; Eye Care; USA; Jul. 2004.

http://www.gnpd.com; Mintel; Advanced-C Skin Tightening Cream; Record ID: 10174541; Cellex-C International; Ceilex-C; Skincare; Face/Neck Care; USA; Jul. 2004.

http://www.gnpd.com; Timeless Night Overnight Age Relief Spray; Record ID: 10181727; Erno Laszlo; Erno Laszlo; Skincare; Body Care; USA; Aug. 2004.

http://www.gnpd.com; Mintel; Face Cream; Record ID: 10104993; Hope Aesthetics; Hope Aesthetics Hope's Answer; Skincare; Face/Neck Care; USA; Mar. 2002.

PCT International Search Report; International Application No. PCT/US2008/063610; Completion Date: Oct. 22, 2008; Date of Mailing: Oct. 22, 2008.

PCT Written Opinion of the International Searching Authority, or the Declaration; International Application No. PCT/US2008/063610; Completion Date: Oct. 22, 2008; Date of Mailing: Oct. 22, 2008.

PCT International Search Report; International Application No. PCT/US2008/075210; Completion Date: Mar. 23, 2009; Date of Mailing: Mar. 23, 2009.

PCT Written Opinion of the International Searching Authority, or the Declaration; International Application No. PCT/US2008/075210; Completion Date: Mar. 23, 2009; Date of Mailing: Mar. 23, 2009.

Scapagnini, et al.; Forum Original Research Communication; "Ethly Ferulate, a Lipophilic Polyphenol, Induces HO-1 and Protects Rat Neurons Against Oxidative Stress," Antioxidants & Redox Signaling; vol. 6; No. 5; pp. 811-818; Oct. 2004.

http://www.sigma-aldrich.com/catalog/search/ProductDetail/SIGMA/P1499?PrtPrv=1&I . . . ; P1499 Pterostilbene; Jul. 2007.

Prottey, et al; "The repair of impaired epidermal barrier function in rats by the cutaneous application of linoleic acid;" British Journal of Dermatology; vol. 94; pp. 13-21; 1976.

Supplemental European Search Report; EP08829394; Completion Date: Feb. 20, 2015; Mailing Date: Mar. 2, 2015.

Supplemental European Search Report; EP08755460.6; Completion Date: May 11, 2015; Mailing Date: May 15, 2015.

Kesinger, et al.; Review; Covalent interaction of ascorbic acid with natural products; Phytochemistry 70; 2009, pp. 1930-1939.

\* cited by examiner

US 9,220,669 B2

RESVERATROL FERULATE COMPOUNDS, COMPOSITIONS CONTAINING THE COMPOUNDS, AND METHODS OF USING THE SAME

CROSS-REFERENCE TO RELATED APPLICATIONS

This is a divisional of U.S. patent application Ser. No. 12/204,064 filed Sep. 4, 2008 now abandoned, which claims priority to U.S. Provisional Patent Application No. 60/970,943 filed on Sep. 8, 2007 and U.S. Provisional Patent Application No. 61/029,600 filed on Feb. 19, 2008.

FIELD OF THE INVENTION

The present invention relates to new chemical compounds as well as to cosmetic or pharmaceutical compositions containing such new compounds. More specifically, the present invention relates to resveratrol ferulate compounds and compositions containing such compounds in a cosmetically or pharmaceutically acceptable carrier for achieving skin lightening, anti-aging, and antioxidant effects. The compositions of the present invention exhibit not only excellent skin lightening, anti-aging, and antioxidant effects, but also surprising and unexpected color stability and extended shelf life.

BACKGROUND OF THE INVENTION

The human skin is variously colored, showing individual variations even within racial groups. The appearance of the skin is mainly determined by melanin, a pigment manufactured by melanocytes which are found among the basal cells of the epidermis.

Melanin is a water-insoluble polymer of various compounds derived from the amino acid tyrosine. It is one of two pigments found in human skin and hair and adds brown to skin color; the other pigment is carotene which contributes yellow coloring. The synthesis of melanin reactions is catalyzed by the enzyme tyrosinase. Tyrosinase is found in only one specialized type of cell, the melanocyte, and in this cell melanin is found in membrane-bound bodies called melanosomes. The various hues and degrees of pigmentation found in the skin of human beings are directly related to the number, size, and distribution of melanosomes within the melanocytes and other cells. Besides its role in pigmentation, melanin, which absorbs ultraviolet light, plays a protective role when skin is exposed to the damaging rays of the sun. It is melanin, produced in response to the stimulus of UV light, which is responsible for the tanning of the skin.

Although the heterogeneous distribution of melanin in the skin, for example, in the form of freckles or moles, is considered by some as a defining characteristic of beautiful skin, such "beauty marks", on the other hand, often are found to be less desirable by others who seek to lighten these darkened areas of the skin. Even in cases where the skin is homogeneously dark, it is often desired to lighten the skin overall.

Various classes of whitening agents with different skin lightening mechanisms and effects are known. For example, tyrosinase inhibitors, such as kojic acid, interfere with the synthesis of melanin in the melanocytes of the skin, therefore reducing the total amount of melanin in the skin. Certain bleaching agents, such as hydrogen peroxide, hydroquinone, 4-isopropylcatechol and hydroquinone monobenzyl ether, lighten the skin by decomposing or reducing already formed melanin in the skin. Certain exfoliants, such as scorbic acid, salicylic acid and lactic acid, have also been used as whitening agents, and they achieve the skin lightening effects by causing the top layer of the skin to shed. Further, yeast extract or live yeast belonging to the genus *Saccharomyces* has been known to exhibit a melanin-decomposing or melanin-suppressing effect and therefore has been used in whitening compositions.

Resveratrol, also referred to as 3,5,4'-trihydroxystilbene, is a polyhydroxy-substituted compound found in red grapes, raspberries, blueberries, and certain other plant berries or extracts. There has been reports that resveratrol exhibits various anti-cancer, antiviral, anti-aging, skin whitening, and antioxidant effects, and it has been incorporated into a variety of cosmetic formulations, such as skin creams. However, one problem with resveratrol is that it is generally unstable in cosmetic formulations. Accordingly, if used in cosmetic formulas, it can only be used in very small amounts. If present in too large an amount, the resveratrol will hydrolyze and cause the cosmetic formulation into which it is incorporated to become discolored.

Ferulic acid has long been recognized for its skin whitening and antioxidant effects on skin. However, ferulic acid readily undergoes undesirable decomposition at a relatively low temperature and lacks long-term stability. Therefore, formulation of ferulic acid into cosmetic compositions has proven to be generally difficult, due to issues related to product stability and shelf life.

It is an object of the invention to provide new chemical compounds with not only enhanced skin lightening, anti-aging, and antioxidant effects, but also significantly increased color stability and extended shelf life, which can be readily formulated into various cosmetic or pharmaceutical compositions for topical, oral, transdermal, intravenous, intramuscular, intraperitoneal, intrasternal, subcutaneous, intraarticular, intranasal, sublingual, pulmonary, or rectal administration.

It is a further object of the invention to provide aesthically pleasing and stable cosmetic compositions that are commercially acceptable.

SUMMARY OF THE INVENTION

In one aspect, the present invention relates to a method for skin lightening, preventing or reducing skin aging, and/or reducing reactive oxygen species in the skin comprising applying to the skin a cosmetic composition comprising an ester of resveratrol with an aliphatic or aromatic carboxylic acid in a topically or cosmetically acceptable carrier. Preferably, but not necessarily, the resveratrol ester is a resveratrol ferulate.

In yet another aspect, the present invention relates to a method for synthesizing resveratrol ferulates comprising: (a) forming a first solution containing resveratrol; (b) forming a second solution containing ferulic acid; (c) forming a third solution containing a liquid-phase acid; (d) mixing the first, second, and third solutions to form a liquid mixture; and (e) heating the liquid mixture to form solid crystals containing resveratrol ferulates.

Other aspects and objectives of the present invention will become more apparent from the ensuing description, examples, and claims.

DETAILED DESCRIPTION OF THE INVENTION, AND PREFERRED EMBODIMENTS THEREOF

Figure 1:
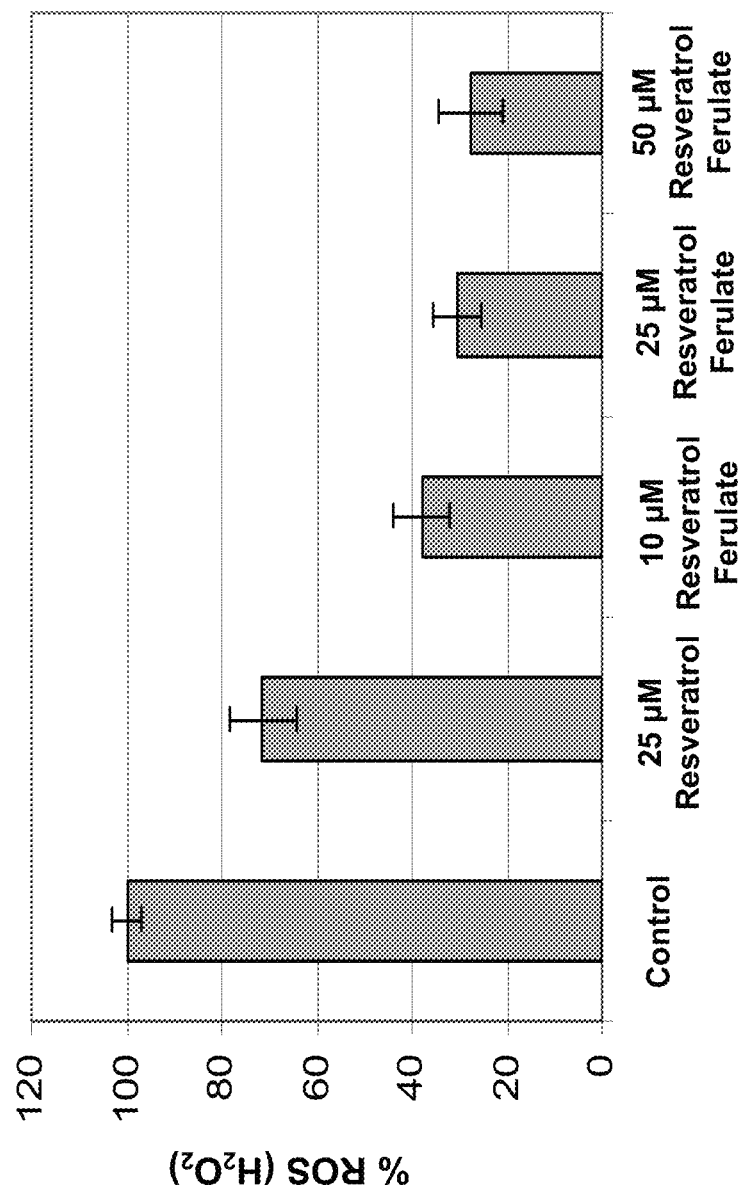
FIG. 1 is a chart showing the relative levels of endogenous reactive oxygen species (ROS) in normal human epidermal keratinocyte (NHEK) cell cultures treated with resveratrol ferulates at various concentrations, in comparison with untreated NHEK cell cultures (control) or NHEK cell cultures treated with resveratrol.

The compositions of the invention may be in the liquid, solid, or semi-solid form. It may be aqueous based, i.e., comprising water or other polar non-aqueous solvents such as mono-, di-, or polyhydric alcohols, glycols, or the ingredients referred to as humectants as set forth below, in addition to the aqueous phase structuring agent. In the case where the compositions are in the form of an aqueous based composition, the composition may comprise from about 0.0001-99%, preferably from about 0.5 to 90%, more preferably from about 0.5 to 85% resveratrol ferulate by weight of the total composition. Alternatively, the compositions of the present invention may have a water-in-oil or oil-in-water emulsion form, i.e., containing both an oil phase and an aqueous phase. In such case, the amount of water may range from about 0.1-99%, preferably from about 5-85%, more preferably from about 7-75% by weight of the total composition. The amount of oil will preferably range from about 1-95%, preferably from about 5-85%, more preferably from about 7-65% by weight of the total composition. More specifically, the resveratrol ferulate may be solubilized or dispersed in either the aqueous base or the oil phase of the emulsion. Further, the compositions of the present invention may be in a non-aqueous or anhydrous form. Anhydrous compositions are formed when the resveratrol ferulate is solubilized or dispersed in a polar non-aqueous solvent such as ethanol, propylene glycol, butylene glycol, or non-polar oils, and the like.

The compositions of the present invention may be cosmetic or pharmaceutical compositions specifically designed for topical application to the skin or keratinous surfaces, such as lips, faces, hands, eye lids, or other bodily surfaces. Exemplary topical cosmetic compositions may include various color cosmetic products, such as lipsticks, blush, eye shadow, eyeliner, lip liner, and nail color; various skin treatment products, such as creams, lotions, serums, gels, mists, and toners; and various rinse-off products, such as cleansers, sprays, masks, and conditioners. Alternatively, the compositions of the present invention may be pharmaceutical compositions suitable for topical administration, which include liquid or semi-liquid preparations, such as liniments, lotions, ointments, creams, or pastes, or drops suitable for administration to the eye, ear, or nose.

The cosmetic or pharmaceutical compositions of the present invent may also be designed for: (1) transdermal administration in form of, e.g., a patch either of the reservoir and porous membrane type or of a solid matrix variety; (2) oral administration in form of, e.g., a tablet, pill, capsule, powder, granule, suspension or liquid; or (3) parenteral injection in form of, e.g., physiologically acceptable, sterile aqueous or nonaqueous solutions, dispersions, suspensions, or emulsions and sterile powders for reconstitution into sterile injectable solutions or dispersions. Note that the foregoing is merely illustrative of the invention and is not intended to limit the invention to the disclosed delivery mechanisms. Variations and changes which are obvious to one skilled in the art are intended to be within the scope and nature of the invention which are defined in the appended claims.

I. Resveratrol Ferulates

Resveratrol ferulate compounds of the invention have a general formula of:

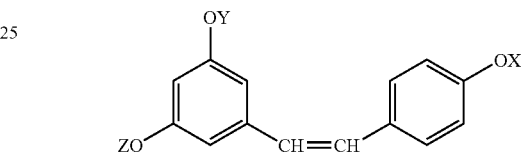

wherein X, Y, and Z are either hydrogen or a feruloyl group having a formula of:

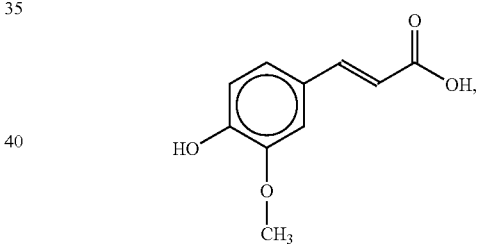

provided that at least one of X, Y, and Z is the feruloyl group.

Therefore, resveratrol ferulates of the present invention may include: (1) mono-ferulates, such as 3-ferulate-5,4'-dihydroxystilbene, 5-ferulate-3,4'-dihydroxystilbene, and 4'-ferulate-3,5-dihydroxystilbene; (2) di-ferulates, such as 3,5-diferulate-4'-hydroxystilbene, 3,4'-diferulate-5-hydroxystilbene, and 4',5-diferulate-3-hydroxystilbene; (3) tri-ferulate, i.e., 3,5,4'-triferulate-hydroxystilbene, and (4) a mixture of mono-, di-, and/or tri-ferulates. Preferably, but not necessarily, the cosmetic compositions of the present invention comprise a mixture of mono-, di-, and/or tri-ferulates.

The resveratrol ferulates of the present invention have significantly enhanced color stability and extended shelf life, in comparison with either resveratrol or ferulic acid or a simple mixture thereof. Although not wishing to be bound by any specific theory, it is believed that upon application to the human skin, resveratrol, ferulates as described hereinabove may be readily hydrolyzed by endogenous esterase enzymes in the human skin to release active resveratrol and ferulic acid. Further, since the enzymatic hydrolysis reaction is a rate-limited process, resveratrol and ferulic acid are released slowly over time from the cosmetic compositions of the present invention to achieve extended skin lightening effects.

The resveratrol ferulates of the present invention can be synthesized by various processes well known in the art. For example, resveratrol ferulates can be formed by a liquid-phase esterification reaction between resveratrol and ferulic acid, in which a liquid phase acid, such as sulfuric acid, phosphoric acid, sulfonic acid, or p-toluene sulfonic acid, is utilized as the catalyst. For another example, resveratrol ferulates can be formed through a condensation reaction between resveratrol and ferulic acid in the presence of a coupling agent and a weakly nucleophilic basic catalyst. The coupling agent, such as dicyclohexylcarbodiimide, functions to activate the ferulic acid by converting it into anhydride equivalent. The basic catalyst, such as 4-dimethylaminopyridine (DMAP), functions to catalyze the reaction between the hydroxyl groups of resveratrol and the carboxylic acid group of the ferulic acid anhydride. For yet another example, resveratrol can be reacted with a relatively more reactive derivative of ferulic acid, such as feruloyl chloride or the anhydride form of ferulic acid, to form the resveratrol ferulates through the well-known Schotten-Baumann reaction in an alkaline aqueous solution. Such an alkaline aqueous solution typically contains a base, which functions both as a catalyst and a trap for the inorganic acid byproduct formed by the reaction (e.g., HCl when feruloyl chloride is used). Specifically, pyridine can be used for solubilizing or dispersing the resveratrol, since it can serve simultaneously as the reaction solvent, the catalyst and the trap for the acid released by the reaction. When pyridine is used, the reaction can readily proceed at ambient temperature under sufficient agitation. For still a further example, resveratrol can first be solubilized or dispersed in a liquid medium containing a chlorinated solvent, such as chloroform or methylene chloride, followed by addition of an aliphatic tertiary amine of low boiling point (e.g., triethylamine or TEA) in the presence of an organic base such as DMAP. The feruloyl chloride can then be introduced slowly into the mixture at a relatively low temperature (e.g., less than 40° C.) and under agitation to form resveratrol ferulates.

Preferably, but not necessarily, resveratrol ferulates as used in the present invention are formed by a liquid-phase esterification reaction between resveratrol and ferulic acid using p-toluene sulfonic acid as the catalyst.

The resveratrol ferulates may be present ranging from about 0.001 to 95%, preferably from about 0.005 to 90%, more preferably from about 0.1 to 20% by weight of the total composition.

The biological activities of the resveratrol ferulates of the present invention can be further enhanced or increased through a bioconversion process, such as, for example, by incubating the resveratrol ferulates in the presence of yeast or other suitable microorganisms, under suitable aerobic conditions, for a sufficient period of time. The bioconversion process can take either one of two approaches. The first approach is a process in which the microorganism is incubated not only with resveratrol ferulates of the present invention, but also with traditional culturing nutrients, which provide suitable conditions not only for the microorganism to conduct the desired bioconversion, but also for it to multiply. The second, and preferred, approach is to incubate the microorganism in an aqueous environment, in the presence of only resveratrol ferulates and in the substantial absence of any additional nutrients other than resveratrol ferulates. During this method of processing, the microorganism does not multiply but only engages in the catabolic processing of the resveratrol ferulates. The bioconversion is monitored periodically for signs of the plateauing of biological activity, for example, a leveling off of pH, and then the system temperature is raised to between about 30-50° C., preferable about 40-45° C., for at least about 24 hours. In one embodiment, the temperature is then briefly raised to 90-95° C. for a period of about 5-10 minutes, which ruptures the microorganism, releasing the cell contents. Alternately, the cells can be disrupted by sonication. The entire system is then cooled to room temperature, and filtered with progressively decreasing pore size to remove yeast debris, leaving a fermentation extract of resveratrol ferulates that has an enhanced level of biological activities in comparison with un-fermented resveratrol ferulates. The microorganism used for such bioconversion of the resveratrol ferulates can be any microorganism that is normally used for bioconversion purposes. A particularly useful microorganism is a standard brewer's yeast, *Saccharomyces cerevisiae*. Nevertheless, other aerobic microorganisms, including, but not limited to: *Aspergillus nidulans, Saccharomyces pombe, Thermus aquaticus, Bacillus subtilis*, cyanobacteria, or archaebacteria, can also be used.

Preferably, but not necessarily, the resveratrol ferulates are encapsulated in one or more vesicles, microspheres, nanospheres, capsules, or mixtures thereof. Such vesicles, microspheres, nanospheres, or capsules form a trans-dermal delivery system for more effective delivery of the resveratrol ferulate through the epidermis layer into the dermis layer of the skin. Further, such delivery system may provide targeted delivery and sustained release of the resveratrol ferulate at the active sites, e.g., in the dermis layer of the skin.

Liposomes, which are microscopic vesicles consisting of an aqueous core enclosed in one or more lipid layers, can be used for encapsulating the resveratrol ferulate to facilitate delivery thereof into the dermis. Naturally-occurring membrane lipids, such as phospholipids and sphingomyelins, have been widely used for formation of liposomes. Certain synthetic lipids capable of spontaneous formation of liposomes upon addition into an aqueous solution have also been developed recently. For example, diacylglycerol-polyethyleneglycol (PEG) compounds, such as PEG-12 glycerol dimyristate, PEG-12 glycerol dioleate, PEG-23 glycerol dipalmitate, PEG-12 glycerol distearate, and PEG-23 distearate, have been used for spontaneous formation of non-phospholipid-based liposomes, as described in greater detail by U.S. Pat. Nos. 7,150,883; 6,958,160; and 6,610,322, the contents of which are incorporated herein by reference in their entireties for all purposes. Such non-phospholipid-based liposomes are commercially available from Corwood Laboratories (Hauppauge, N.Y.) under the trade name of QuSomes™.

Microspheres and/or nanospheres formed of biocompatible (more preferably, biodegradable) materials can also be employed for encapsulating the resveratrol ferulates of the present invention to achieve targeted delivery and/or sustained release thereof. The term "biocompatible" as used herein refers to any material, composition, structure, or article that having essentially no toxic or injurious impact on the living tissues or living systems which the material, composition, structure, or article is in contact with and produce essentially no immunological response in such living tissues or systems. More particularly, the material, composition, structure, or article has essentially no adverse impact on the growth and any other desired characteristics of the cells of the living tissues or living systems that are in contact with the material, composition, structure, or article. Generally, methods for testing the biocompatibility of a material, composition, structure, or article is well known in the art. The term "biodegradable" as used herein refers to any material, composition, structure, or article that will degrade over time by action of enzyme, hydrolytic reaction, and/or similar mechanisms in the body of a living organism.

For example, U.S. Patent Application Publication No. 2004/0109894, the content of which is incorporated herein by reference in its entirety for all purposes, describes various matrix materials with good biocompatibility and sufficient barrier properties for formation of hydrophobic nanospheres. Such matrix materials include, for example, natural waxes, synthetic waxes, fats, fatty acids and derivatives thereof, glyceride materials, phospholipids, steroids, tocopherol and derivatives thereof, hydrogenated or derivatized oils. It also describes various pH- and salt-sensitive matrix materials that can be used for formation of pH-sensitive or salt-sensitive microspheres. Exemplary pH- and salt-sensitive matrix materials include, but are not limited to: copolymers of acrylate polymers with amino substituents, acrylic acid esters, polyacrylamides, phthalate derivatives such as acid phthalates of carbohydrates, amylose acetate phthalate, amylose acetate phthalate, cellulose acetate phthalate, other cellulose ester phthalates, cellulose ether phthalates, hydroxy propyl cellulose phthalate, hydroxypropyl ethylcellulose phthalate, hydroxypropyl methyl cellulose phthalate, methyl cellulose phthalate, polyvinyl acetate phthalate, polyvinyl acetate hydrogen phthalate, sodium cellulose acetate phthalate, starch acid phthalate, styrene-maleic acid dibutyl phthalate copolymer, styrene-maleic acid polyvinyl acetate phthalate copolymer, styrene and maleic acid copolymers, formalized gelatin, gluten, shellac, salol, keratin, keratin sandarac-tolu, ammoniated shellac, benzophenyl salicylate, cellulose acetate trimellitate, cellulose acetate blended with shellac, hydroxypropylmethyl cellulose acetate succinate, oxidized cellulose, polyacrylic acid derivatives such as acrylic acid and acrylic ester copolymers, methacrylic acid and esters thereof, vinyl acetate and crotonic acid copolymers. Further, U.S. Patent Application Publication No. 2004/0109894 describes the use of various water-soluble polymers for formation of water-sensitive microspheres. Exemplary water-soluble polymers include, but are not limited to: polyvinyl pyrrolidone (PVP), water soluble celluloses, polyvinyl alcohol (PVA), ethylene maleic anhydride copolymer, methyl vinyl ether maleic anhydride copolymer, polyethylene oxides, water soluble polyamide or polyester, copolymers or homopolymers of acrylic acid such as polyacrylic acid, polystyrene acrylic acid copolymers or starch derivatives, polyvinyl alcohol, polysaccharides, hydrocolloids, natural gums, proteins, and mixtures thereof. Such nanospheres, microspheres, or a combination of nanospheres and microspheres are commercially available from Salvona Technology (Dayton, N.J.) under the trade names of SalSeal™, HydroSal™, NanoSal™, and MultiSal™.

Hyaluronic acid, which is a mucopolysaccharide that exists naturally in all living organisms, can be formulated into microspheres for encapsulation of resveratrol ferulates of the present invention. Specifically, U.S. Pat. No. 6,969,531, the content of which is incorporated herein by reference in its entirety for all purposes, describes microspheres formed by hyaluronic acid functionalized with a homobifunctional crosslinker at glucuronic acid sites for intramolecular and intermolecular cross-linking. Such hyalurnoic filling microspheres, which are commercially available from BASF (Florham Park, N.J.), are provided and delivered to the skin in a dehydrated state initially. Once in contact with the skin moisture, such microspheres rehydrate and expand volumetrically to help stretch the dermal layer of the skin and thereby achieve wrinkle reduction effects.

Cyclodextrins and its derivatives may also be used to form micelles or nanoparticles for encapsulation of resveratrol ferulates of the present invention. Specifically, U.S. Pat. No. 6,524,595, the content of which is incorporated herein by reference in its entirety for all purposes, describes a group of non-hydroxyalkylated cyclodextrin derivatives that can be used to form nanoparticles with excellent tissue or membrane penetration properties for targeted delivery of the active ingredients encapsulated therein. Such cyclodextrin-based nanoparticles are commercially available from BASF (Florham Park, N.J.) under the trade name of Cyclocaps®.

Deoxyribonucleic acid (DNA) molecules, ribonucleic acid (RNA) molecules, or oligonucleotides can also be used for forming microspheres or microcapsules for encapsulation of the resveratrol ferulate of the present invention. Such biopolymers are sensitive to UV radiation and can therefore be employed to form UV-sensitive microspheres or microcapsules for targeted delivery of active ingredients upon UV radiation, as described by U.S. Patent Application Publication No. 2004/0121019, the content of which is incorporated herein by reference in its entirety for all purposes. Such UV-sensitive delivery system is commercially available from BASF (Florham Park, N.J.) under the trade name of SmartVector® UV.

U.S. Pat. No. 5,736,161 describes a delivery system comprising a gellable hydrocolloid core with a cationic polysaccharide coating. The hydrocolloid core may contain materials such as silica or starch, while the cationic polysaccharide coating may be formed of dextrins or derivatives thereof. Such a delivery system is commercially available from LipoTec (Barcelona, Spain) under the trade name of Thermospheres-15.

Various biopolymer-based microspheres commercially available from BASF (Florham Park, N.J.) under the trade names of Phytosphere®, Thalasphere®, Thalachitosphere®, and Collasphere® can also be used for encapsulation and delivery of the resveratrol ferulates of the present invention.

II. Other Resveratrol Esters

The cosmetic or pharmaceutical compositions of the present invention may employ other resveratrol esters derived from resveratrol and other carboxylic acids exhibiting similar skin lightening and/or antioxidant effects as ferulic acid, in addition to the resveratrol ferulates. For example, the compositions of the present invention may comprise esters of resveratrol with one or more carboxylic acids that are known to be used for skin whitening or other purposes, which include but are not limited to: cinnamic acid, glycolic acid, lipoic acid, gluconic acid, citric acid, lactic acid, azelaic acid, hydroxy-substituted benzoic acids, genistic acid, hydroxycaprylic acid, linoleic acid, salicylic acid, 5-octanoyl salicylic acid, tranexamic acid, and derivatives thereof. Such other resveratrol esters can be used in addition to the resveratrol ferulates described hereinabove in the compositions of the present invention.

III. Other Ingredients

The cosmetic or pharmaceutical compositions of the present invention may contain other ingredients, including structuring agents, oils, preservatives, humectants, and the like. The compositions may be in the anhydrous form, or in the form of emulsions, gels, serums, solutions, or suspensions. If in the emulsion form, water-in-oil or oil-in-water emulsions are suitable. If in the aqueous form the water may be present in amounts ranging from about 0.1 to 99%, preferably from about 0.5 to 90%, more preferably from about 1 to 85% by weight of the total composition.

A. Aqueous Phase Structuring Agents

In the event that the topical compositions of the invention contain an aqueous phase, the compositions may contain at least one aqueous phase structuring agent, that is an agent that increases the viscosity or, or thickens, the aqueous phase of the composition. The aqueous phase structuring agent is compatible with the resveratrol ferulate compound and the other ingredients in the formulation. Suitable ranges are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like.

1. Polysaccharides

A variety of polysaccharides may be suitable aqueous phase thickening agents. Examples of such polysaccharides include naturally derived materials such as agar, agarose, alicaligenes polysaccharides, algin, alginic acid, *acacia* gum, amylopectin, chitin, dextran, *cassia* gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

2. Acrylate Polymers

For example, acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

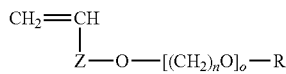

wherein Z is —$(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula $CH_2$=$CR'CH_2OB_nR$, in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where W denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly)ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 alkyl ether (40/50/10).

Also suitable are acrylate copolymers such as Polyacrylate-3 which is a copolymer of methacrylic acid, methylmethacrylate, methylstyrene isopropyl isocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

Particularly suitable as the aqueous phase thickening agent are acrylate based polymeric thickeners sold by Clariant under the Aristoflex trademark such as Aristoflex AVC, which is ammonium acryloyldimethyltaurateNP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

3. High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

B. Oil Phase Structuring Agents

A variety of oil phase structuring agents may optionally be present in the oil phase of the cosmetic compositions when the compositions are in emulsion or anhydrous form. The term "oil phase structuring agent" means an ingredient or combination of ingredients, soluble or dispersible in the oil phase, which will increase the viscosity, or structure, the oil phase. The oil phase structuring agent is compatible with the resveratrol derivative and the rest of the formulation ingredients. The term "compatible" means that the oil phase structuring agent and resveratrol derivative are capable of being formulated into a cosmetic product that is generally stable. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both.

1. Silicone Structuring Agents

A variety of oil phase structuring agents may be silicone based, such as silicone elastomers, silicone gums, silicone waxes, linear silicones having a degree of polymerization that provides the silicone with a degree of viscosity such that when incorporated into the cosmetic composition it is capable of increasing the viscosity of the oil phase. Examples of silicone structuring agents include, but are not limited to:

(a). Silicone Elastomers

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or non-volatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crossopolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252 to Sakuta et al., issued Nov. 13, 1990; U.S. Pat. No. 5,760,116 to Kilgour et al., issued Jun. 2, 1998; U.S. Pat. No. 5,654,362 to Schulz, Jr. et al. issued Aug. 5, 1997; and Japanese Patent Application JP 61-18708, assigned to Pola Kasei Kogyo KK, each of which are herein incorporated by reference in its entirety.

(b). Silicone Gums

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all sub-ranges, e.g. 550,000; 925,000; 3.5 million.

The silicone gums that are used in the compositions include, but are not limited to, those of the general formula wherein:

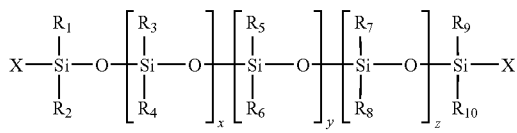

$R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

(c). Silicone Waxes

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

(d). Polyamides or Silicone Polyamides

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

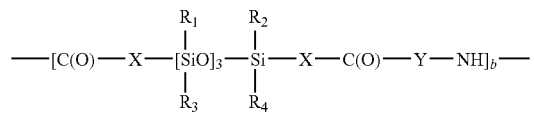

X is a linear or branched alkylene having from about 1-30 carbon atoms;

$R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

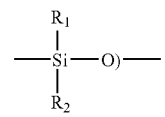

and Y is:

(a) a linear or branched alkylene having from about 1-40 carbon atoms which may be substituted with (i) one or more amide groups having the general formula $R_1CONR_1$, or (ii) $C_{5-6}$ cyclic ring, or (iii) phenylene which may be substituted with one or more $C_{1-10}$ alkyl groups, or (iv) hydroxy, or (v) $C_{3-8}$ cycloalkane, or (vi) $C_{1-20}$ alkyl which may be substituted with one or more hydroxy groups, or (vii) $C_{1-10}$ alkyl amines; or (b) $TR_5R_6R_7$ wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

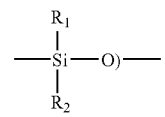

Preferred is where $R_1$, $R_2$, $R_3$, and $R_4$ are $C_{1-10}$, preferably methyl; and X and Y is a linear or branched alkylene. Preferred are silicone polyamides having the general formula:

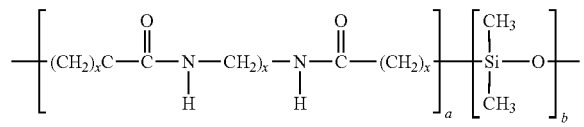

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether.

Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

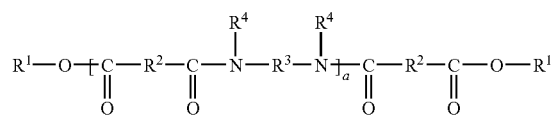

wherein n denotes a number of amide units such that the number of ester groups ranges from about 10% to 50% of the total number of ester and amide groups; each $R_1$ is independently an alkyl or alkenyl group containing at least 4 carbon atoms; each $R_2$ is independently a $C_{4-42}$ hydrocarbon group, with the proviso that at least 50% of the $R_2$ groups are a C30-42 hydrocarbon; each $R_3$ is independently an organic group containing at least 2 carbon atoms, hydrogen atoms and optionally one or more oxygen or nitrogen atoms; and each $R_4$ is independently a hydrogen atom, a $C_{1-10}$ alkyl group or a direct bond to $R_3$ or to another $R_4$, such that the nitrogen atom to which $R_3$ and $R_4$ are both attached forms part of a heterocyclic structure defined by $R_4$—N—$R_3$, with at least 50% of the groups $R_4$ representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

(f). Natural or Synthetic Organic Waxes

Also suitable as the oil phase structuring agent may be one or more natural or synthetic waxes such as animal, vegetable, or mineral waxes. Preferably such waxes will have a higher melting point such as from about 60 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, *acacia*, beeswax, ceresin, cetyl esters, flower wax, *citrus* wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

(g). Montmorillonite Minerals

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

(h). Silicas and Silicates

Another type of structuring agent that may be used in the oil phase of the composition is silica, silicates, or silica sylylate, and alkali metal or alkaline earth metal derivatives thereof. These silicas and silicates are generally found in the particulate form and include silica, silica silylate, magnesium aluminum silicate, and the like.

C. Oils

The cosmetic compositions of the present invention may contain an oil phase with one or more oils, such as nonvolatile silicone oils, volatile silicones, esters, vegetable oils, or synthetic oils. The oils used in the compositions of the invention are preferably pourable liquids at room temperature.

1. Non-Volatile Silicone Oil

In the embodiment where the composition is in emulsion form, the oil phase preferably contains one or more nonvolatile silicone oils. The term "nonvolatile" means that the silicone oil has a vapor pressure of less than about 2 mm. of mercury at 25° C. The silicone oil may be water soluble or water insoluble, but is preferably water insoluble. Suitable ranges include from about 0.01 to 80%, preferably from about 0.1 to 60%, more preferably from about 0.5 to 40% by weight of the total composition. Such silicones preferably have a viscosity ranging from greater than about 5 to 800,000 cst, preferably 10 to 200,000 cst at 25° C. Suitable silicones include amine functional silicones such as amodimethicone; phenyl substituted silicones such as bisphenylhexamethicone, trimethylsiloxyphenyl dimethicone, phenyl trimethicone, or polyphenylmethylsiloxane; dimethicone, dimethicone substituted with $C_{2-30}$ alkyl groups such cetyl dimethicone, or fluorinated silicones such as trifluoropropyl dimethicone.

Nonvolatile silicones may have the following general formula:

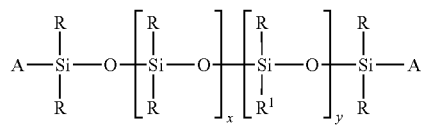

wherein R and R' are each independently $C_{1-30}$ straight or branched chain, saturated or unsaturated alkyl, phenyl or aryl, trialkylsiloxy, and x and y are each independently 0 to 1,000, 000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the tradenames Abil Wax 9801, or 9814.

2. Volatile Silicones

The term "volatile" means that the oil has a measurable vapor pressure, or a vapor pressure of at least about 2 mm. of mercury at 20° C. Suitable volatile oils that may be used in the compositions generally have a viscosity ranging from about 0.5 to 5 centistokes 25° C. and include linear silicones, cyclic silicones, paraffinic hydrocarbons, or mixtures thereof.

Cyclic silicones are of the general formula:

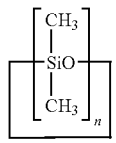

where n=3-6.

Linear volatile silicones in accordance with the invention have the general formula:

$(CH_3)_3Si-O-[Si(CH_3)_2-O]_n-Si(CH_3)_3$ where n=0, 1, 2, 3, 4, or 5, preferably 0, 1, 2, 3, or 4.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, dodecamethylcyclohexasiloxane and the like. Also suitable are linear volatile silicones such as hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof.

3. Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

4. Non Silicone Nonvolatile Oils

A variety of nonvolatile oils other than silicones are also suitable for use in the cosmetic compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

(a). Esters

Suitable esters are mono-, di-, and triesters. The composition may comprise one or more esters selected from the group, or mixtures thereof.

(i) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(ii). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(iii). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described on pages 1670-1676 of the C.T.F.A. Cosmetic Ingredient Dictionary and Handbook, Eighth Edition, 2000, which is hereby incorporated by reference in its entirety.

(b). Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

(c). Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, *camelina sativa* oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisoteatate, glyceryl tetraisostearate, glyceryl trioctanoate, diglyceryl disteatate, glyceryl linoleate, glyceryl myristate, glyceryl isostearate, PEG castor oils, PEG glyceryl oleates, PEG glyceryl stearates, PEG glyceryl tallowates, and so on.

(d). Fluorinated Oils

Various types of fluorinated oils may also be suitable for use in the compositions including but not limited to fluorinated silicones, fluorinated esters, or perfluoropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers include those disclosed in U.S. Pat. Nos. 5,183,589, 4,803,067, 5,183,588 all of which are hereby incorporated by reference, which are commercially available from Montefluos under the trademark Fomblin.

D. Surfactants

The composition may contain one or more surfactants, which may be silicone or organic. The surfactants will aid in the formation of stable emulsions of either the water-in-oil or oil-in-water form. If surfactants are present in anhydrous formulations, they may aid in dispersion of pigments or other polar materials. If present, the surfactant may range from about 0.001 to 30%, preferably from about 0.005 to 25%, more preferably from about 0.1 to 20% by weight of the total composition.

1. Silicone Surfactants

Suitable silicone surfactants include polyorganosiloxane polymers that have amphiphilic properties, for example contain hydrophilic radicals and lipophilic radicals. These silicone surfactants may be liquids or solids at room temperature.

(a). Dimethicone Copolyols or Alkyl Dimethicone Copolyols

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

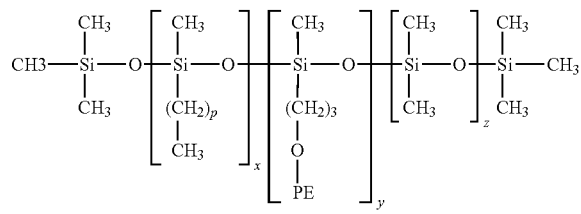

wherein p is 0-40 (the range including all numbers between and subranges such as 2, 3, 4, 13, 14, 15, 16, 17, 18, etc.), and PE is (—$C_2H_4O$)$_a$—(—$C_3H_6O$)$_b$—H wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the tradename Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by. Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

(b). Crosslinked Silicone Surfactants

Also suitable are various types of crosslinked silicone surfactants are referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organopolysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986 and U.S. Pat. No. 5,412,004, U.S. Pat. No. 5,837,793 and U.S. Pat. No. 5,811,487, the contents of which are incorporated by reference.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer.

2. Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are formed by the reaction of a carboxylic acid with an alkylene oxide or with a polymeric ether. The resulting products have the general formula: where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula: wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, preferably $C_{12-22}$ fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

E. Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include mono-, di-, or polyhydric alcohols. Examples of monohydric alcohols, include $C_{2-10}$ alkanols such as ethanol, propanol, butanol, pentanol, hexanol and the like. Glycols such as C2-6 alkylene glycols include ethylene glycol, propylene glycol, butylene glycol, pentylene glycol, and the like. Also suitable are polyhydric alcohols such as sugars glucose, fructose, galactose, mannose, etc. Suitable glycols may also be in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Further examples of such sugars include fructose, honey, hydrogenated honey, inositol, maltose, mannitol, maltitol, sorbitol, sucrose, xylitol, xylose, and so on. Preferably, the humectants used in the composition of the invention are $C_{1-6}$, preferably $C_{2-4}$ alkylene glycols, most particularly butylene glycol.

F. Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *padica pavonica* extract, *thermus thermophilis* ferment extract, *camelina sativa* seed oil, *boswellia serrata* extract, olive extract, *aribodopsis thaliana* extract, *acacia dealbata* extract, *acer saccharinum* (sugar maple), *acidopholus, acorus, aesculus, agaricus, agave, agrimonia,* algae, *aloe, citrus, brassica,* cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Malus, Saxifraga Sarmentosa, Vilis Vinifera, Morus Nigra, Scutellaria Baicalensis, Anthemis Nobilis, Salvia Sclarea, Rosmarinus Officianalis, Citrus Medica Limonum, Panax Ginseng,* and mixtures thereof.

G. Sunscreens

It may also be desirable to include one or more sunscreens in the compositions of the invention. Such sunscreens include chemical UVA or UVB sunscreens or physical sunscreens in the particulate form.

1. UVA Chemical Sunscreens

If desired, the composition may comprise one or more UVA sunscreens. The term "UVA sunscreen" means a chemical compound that blocks UV radiation in the wavelength range of about 320 to 400 nm.

One preferred group of UVA sunscreens are dibenzoylmethane compounds having the general formula:

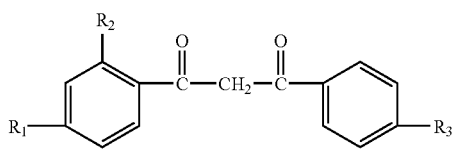

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4' diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

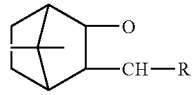

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

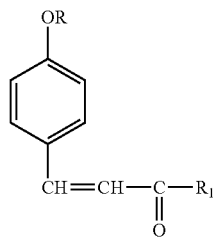

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula: wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

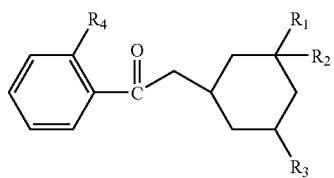

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomethyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

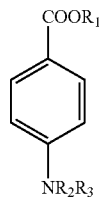

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-50, preferably about 2-45, most preferably about 5-30. Calculation of SPF values is well known in the art. Preferably, the claimed compositions have SPF values greater than 4.

H. Particulate Materials

The compositions of the invention may contain particulate materials in the form of pigments, inert particulates, or mixtures thereof. If present, suggested ranges are from about 0.1-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

1. Powders

The particulate matter may be colored or non-colored (for example white) non-pigmentatious powders. Suitable non-pigmentatious powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

2. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

I. Preservatives

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition is free of parabens.

J. Vitamins and Antioxidants

The compositions of the invention, may contain vitamins and/or coenzymes, as well as antioxidants. If so, 0.001-10%, preferably 0.01-8%, more preferably 0.05-5% by weight of the total composition are suggested. Suitable vitamins include ascorbic acid and derivatives thereof, the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients which assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

III. The Cosmetic or Pharmaceutical Compositions

Topical cosmetic compositions containing the resveratrol ferulate compound may be found in a variety of forms, such as aqueous-based formulas, emulsions, anhydrous formulas, skin creams, gels, lotions, or color cosmetic compositions, such as foundation makeup, lip color, lip liner, blush, eye shadow, and the like. If the topical cosmetic compositions are in form of an emulsion, the resveratrol ferulate may be found either in the aqueous phase or the oil phase of the emulsion. If the compositions are in the form of an anhydrous formula, the resveratrol ferulate may also be dispersed or solubilized in a non-aqueous polar solvent phase of the anhydrous formula. Typical skin creams or lotions comprise from about 5-98% water, 1-85% oil, and from about 0.1 to 20% of one or more surfactants. Preferably the surfactants are nonionic and may be in the form of silicones or organic nonionic surfactants. Typical color cosmetic compositions such as foundations, blush, eyeshadow and the like will preferably contain from about 5-98% water, 1-85% oil, and from about 0.1 to 20% of one or more surfactants in addition to from about 0.1 to 65% of particulates that are pigments or a combination of pigments and powders. The cosmetic compositions of the invention may be found in a wide variety of other forms suitable for topical application.

For oral administration, the compositions containing resveratrol ferulate may be in the form of, for example, a tablet, pill, capsule, powder, suspension or liquid. More specifically, the resveratrol ferulate of the present invention may be combined with one or more adjuvants appropriate for oral administration; such as lactose, sucrose, starch powder, cellulose esters of alkanoic acids, cellulose alkyl esters, talc, stearic acid, magnesium stearates, magnesium oxide, sodium and calcium salts of phosphoric and sulfuric acids, gelatin, *acacia* gum, sodium alginate, polyvinylpyrrolidone, and/or polyvinyl alcohol, and then tableted or encapsulated for easier administration.

For transdermal administration, the resveratrol ferulate-containing compositions of the present invention may be formulated into a patch either of the reservoir and porous membrane type or of a solid matrix variety. In either case, the active ingredients including resveratrol ferulate is delivered continuously from the reservoir or microcapsules through a membrane into the adhesive layer, which is permeable to the active ingredients and is in direct contact with the skin or mucosa of the recipient.

For parenteral administration, the resveratrol ferulate-containing compositions may be in the form of aqueous or non-aqueous isotonic sterile injection solutions or suspensions. These solutions or suspensions may be prepared from sterile powders or granules using one or more of the carriers or diluents well known for parenteral injection.

For pulmonary administration, the resveratrol ferulate-containing compositions of the present invention may be in form of an aerosol or with an inhaler including dry powder aerosol.

IV. Methods of Application

The methods of application in the present invention will depend on the ultimate intended use of the compositions. The topical cosmetic compositions can be applied locally to selected skin areas with hyperpigmentation, to achieve reduction of hyperpigmentation and anti-aging effect in such selected areas, or provide other benefits. The topical cosmetic compositions can also be applied generally to facial skin or other parts of the human body to achieve general skin lightening, anti-aging, or other desired effects in such parts.

The topical cosmetic compositions of the present invention may be applied to the skin on an as-needed basis, or according to a pre-set schedule. The topical cosmetic compositions of the present invention may be applied directly to clean skin, before application of any moisturizer, foundation, make-up, etc. Alternatively, such compositions can be applied over moisturizer, and optionally over foundation and/or make-up. The amount applied each time, the area of application, the duration of application, and the frequency of application can vary widely, depending on the specific need of the user. For example, the topical cosmetic compositions can be applied for a period of days to months or even years, and at a frequency ranging from about once per week to about five times per day. For another example, the compositions can be applied for a period of about six months and at a frequency ranging from about three times a week to about three times per day, and preferably about once or twice per day.

In one specific embodiment of the present invention, the topical cosmetic composition of the present invention can be formulated as a night cream or a night repair serum, which can be applied to the face of an individual before sleep or a period of bodily reset. In another specific embodiment of the present invention, the topical cosmetic composition of the present invention is formulated as a facial mask, which can be applied to the face before sleep or bodily rest, left thereon for a sufficiently long period of time (e.g., overnight), and then rinsed off.

The invention will be further described in connection with the following examples, which are set forth for the purposes of illustration only.

EXAMPLE 1

Synthesis of Resveratrol Ferulates by Liquid-Phase Esterification 91.3 grams of resveratrol (approximately 0.4 M) was first dissolved in 300 ml of tetrahydrofuran (THF) to form a first solution. 77.7 grams of ferulic acid (approximately 0.4 M) was dissolved in 300 ml of THF to form a second solution. 0.1 gram of p-toluene sulfuric acid was dissolved in 20 ml of THF to form a third solution. The first, second, and third solutions were then transferred into a 1000 ml round-bottom flask equipped with a condenser, followed by addition of 10 ml of benzene. The liquid mixture was heated until boiling, and the boiling was continued under reflux for 5 hours to collect 50 ml of distillate. Next, 50 ml of THF and 10 ml of benzene were added into the liquid mixture, which was continued to be heated under reflux for another 5 hours to collect another 50 ml of distillate. Another 50 ml of THF and 10 ml of benzene were added into the liquid mixture, followed by continuous heating of the liquid mixture under reflux for yet another 5 hours. All the distillate so collected was discarded, and boiling of the liquid mixture was continued to distill off more solvent until the liquid mixture in the flask became viscous, but before any solid phase started to form in it (if a solid phase started to form, add some THF into the liquid mixture to dissolve it). The heat was then turned off, and the contents of the flask were allowed to cool slowly, thereby forming solid crystals in the liquid mixture.

Such solid crystals were separated from the liquid mixture and then rinsed briefly with THF. The resulting solids were subsequently dried and ground into powder, which was continued to be dried at an elevated temperature of about 100° C. under continuous air flow, until the solvent completely evaporated and the resulting product became odorless.

In order to collect more solid product from the remaining liquid mixture, 500 ml of benzene was added into such liquid mixture, which was then cooled in a freezer to allow formation of more solid crystals. Such solid crystals were also separated from the liquid mixture, dried, and ground according to the above description.

The solid crystals were then analyzed by High Performance Liquid Chromatography (HPLC). Several distinctive peaks were observed from the HPLC chart, which were believed to represent mono-, di-, and/or tri-ferulates of resveratrol and their respective isomers. In other words, the end product formed by the reactions described hereinabove was a mixture of resveratrol mono-ferulate, resveratrol di-ferulate, and/or resveratrol tri-ferulate and their respective isomers. Such mixture is therefore jointly to as "Resveratrol Ferulates" and was formulated into various topical or cosmetic compositions as described hereinafter.

EXAMPLE 2

Antioxidant Activity of Resveratrol Ferulates

Resveratrol Ferulates of the present invention demonstrated surprising and expected efficacy in reducing endogenous reactive oxygen species (ROS), primarily hydrogen peroxide ($H_2O_2$), in normal human epidermal keratinocyte (NHEK) cell cultures.

Specifically, NHEK cells were cultured and plated, followed by treatment with Resveratrol Ferulates at concentrations of about 10 µM, 25 µM, and 50 µM. As comparative examples, some NHEK cells were separated treated with resveratrol at a concentration of about 25 µM. Further as control examples, some NHEK cells were maintained without treatment with either Resveratrol Ferulates or resveratrol. Four samples of NHEK cells were provided for each treatment. After overnight incubation of the cell cultures, dichlorodihydrofluorescein diacetate was added thereinto. Dichlorodihydrofluorescein diacetate is a useful fluorogenic reagent for detecting reactive oxygen species in cells. Upon oxidation by the reactive oxygen species, dichlorodihydrofluorescein diacetate becomes the highly green fluorescent dichlorofluorescein, which can be readily detected by fluorescene spectroscopy. For example, a Gemini EM microplate spectrofluorometer commercially available from Molecular Devices at Sunnyvale, Calif. was employed to measure the fluorescence ($Ex_{450}$, $Em_{525}$) of the cell cultures at the 5.5 hour time point, which was used as an indication of the amount of reactive oxygen species (primarily $H_2O_2$) in the cells.

As shown in FIG. 1, the average ROS level measured in the control samples (i.e., untreated NHEK cells) was set to be 100%. The samples treated with Resveratrol Ferulates at 10 µM, 25 µM, and 50 µM demonstrated significantly reduced ROS levels in comparison with the control samples, as well as the samples treated with 25 µM resveratrol. Specifically, the samples treated with 10 µM resveratrol has an average reduction in ROS level of about 62.0% in comparison with the control samples, and the samples treated with 25 µM resveratrol has an average reduction in ROS level of about 69.5% in comparison with the control samples. Therefore, it is clear that Resveratrol Ferulates of the present invention effectively reduced the ROS levels in NHEK cells in a dose-dependent manner and can be used as a potent antioxidant in cosmetic or skin care compositions for topical application in order to reduce the ROS level in the skin. More importantly, Resveratrol Ferulate of the present invention have demonstrated significantly higher efficacy in reducing the ROS levels than resveratrol alone (e.g., by more than two-fold at the same concentration), which is both surprising and unexpected.

EXAMPLE 3

Non-Cytotoxicity of Resveratrol Ferulates

Metabolism in viable cells produces "reducing equivalents" such as NADH or NADPH. These reducing compounds pass their electrons to an intermediate electron transfer reagent that can reduce a tetrazolium product, MTS [(3-(4,5-dimethylthiazol-2-yl)-5-(3-carboxymethoxyphenyl)-2-(4-sulfopheny-1)-2H-tetrazolium], into an aqueous, soluble formazan product. At death, cells rapidly lose the ability to reduce tetrazolium products. The production of the colored formazan product, therefore, is proportional to the number of viable cells in culture. In other words, light absorbance by formazan produced in the cell culture can be used as an indicator of the cell viability.

Specifically, NHEK cells were cultured and plated, followed by treatment with Resveratrol Ferulates at concentrations of about 10 µM 25 µM, and 50 µM. As comparative examples, some NHEK cells were separated treated with resveratrol at concentrations of about 25 µM and 50 µM. Further as control examples, some NHEK cells were maintained without treatment with either Resveratrol Ferulates or resveratrol. Four samples of NHEK cells were provided for each treatment. After overnight incubation of the cell cultures, a MTS solution was added to the cells, and the mixture was incubated for about 3 hours at about 37° C., after which time the amount of formazan produced by the NHEK cells from cellular reduction of MTS was measured by reading the absorbance at 490 nm. The amount of formazan so measured is directly indicative of the relative viability of the respective NHEK cell cultures.

Figure 2:
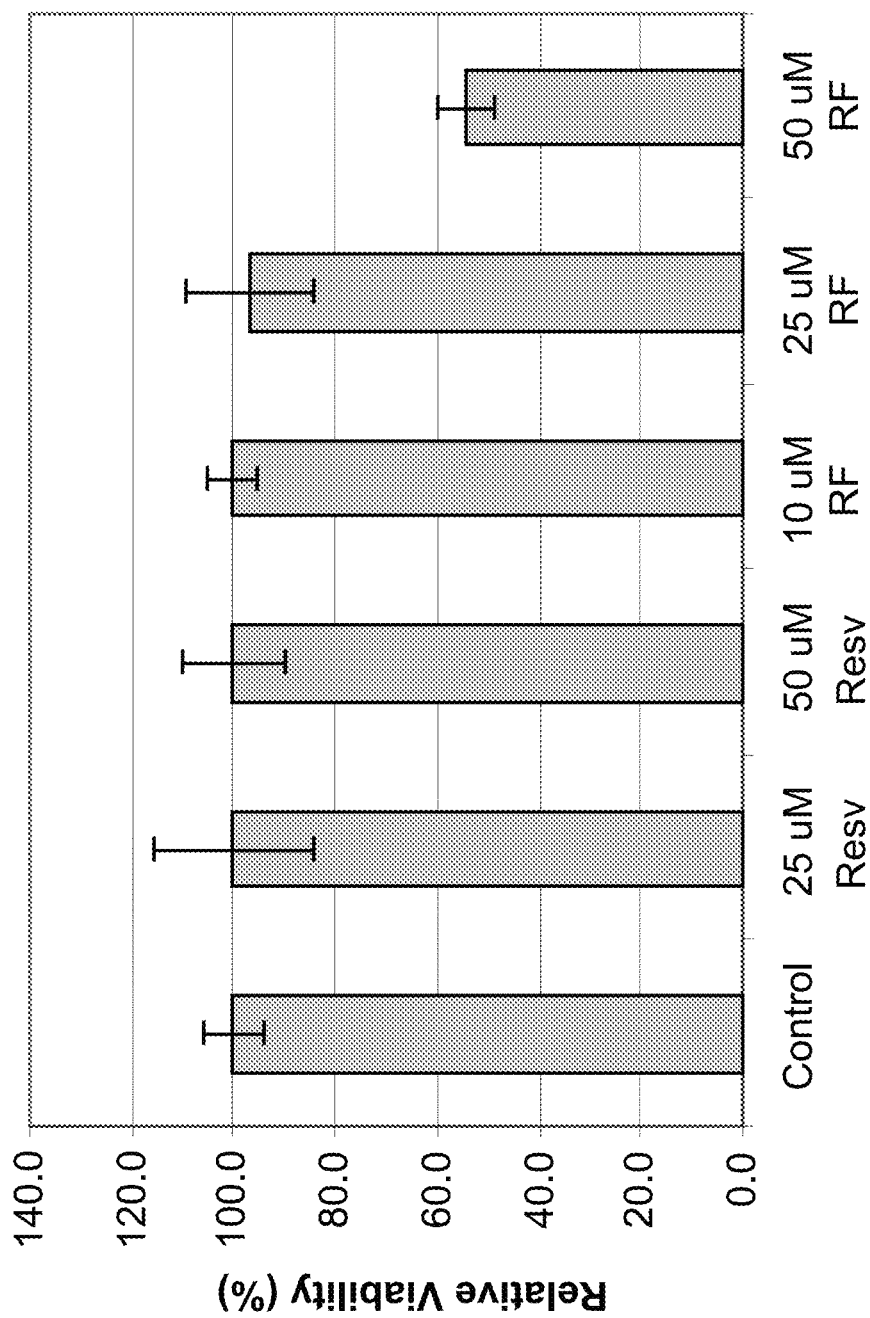
FIG. 2 is a chart showing the relative cell viability of NHEK cell cultures treated with resveratrol ferulates (RF) at various concentrations, in comparison with untreated NHEK cell cultures (control) or NHEK cell cultures treated with resveratrol.

As shown in FIG. 2, the relative cell viability as measured hereinabove for the control samples (i.e., untreated NHEK cells) was set to be 100%. The samples treated with Resveratrol Ferulates at 10 µM and 25 µM maintained the same or similar cell viability as the control samples, indicating that Resveratrol Ferulates are not cytotoxic at 10 µM and 25 µM.

EXAMPLE 4

Resveratrol Ferulates Protected NHEK Cells Against Acute Glycoxidative Stress Caused by Either Methylglyoxal Only or the Combination of Methylglyoxal and UV Light It was previously discovered that exposure of normal human epidermal keratinocytes (NHEK) to a low dose of methylglyoxal (MG) increased the susceptible to UV-induced cell death. Using stress related gene chip analysis, it was also discovered that under such exposure, the antioxidant defense capacity seemed decreased, while genes associated with cell growth arrest and with heat shock protein (HSP) were up-regulated. Because resveratrol ferulates were shown to possess potent antioxidant activity, they were evaluated herein for the protective effect on NHEK cells against exposure to MG alone or combination of MG and UV light. Since resveratrol ferulates of the present invention are esters formed by reaction between resveratrol and ferulic acid, both resveratrol and ferulic acid were separately tested under the same experimental conditions to determine their relative protective effect on NHEK cells against exposure to MG alone or combination of MG and UV.

NHEK cells were cultured at 37° C., 5% $CO_2$, in SFM medium supplemented with EGF 0.25 ng/ml, pituitary extract 25 µg/ml and Gentamycin 25 µg/ml. At sub confluence, the culture medium was replaced with culture medium containing respective actives (i.e., resveratryl ferulates, resveratrol, and ferulic acid) at various concentrations (i.e., 0.5 or 25 µM) and pre-incubated for 1 hour. After incubation, some of the cells were treated with 1 mM of methylglyoxal (MG) for 1 hour. The cells not treated with MG were provided as control samples. Some of the MG-treated cells were then irradiated with UVB (200 mJ/cm$^2$) and UVA (2 J/cm$^2$). The un-irradiated cells were kept in the dark. Six (6) samples of NHEK cells were provided for each treatment described hereinabove. After UV-irradiation, the plates were incubated for 24 hours at 37° C., 5% $CO_2$. Subsequently, the viability was assessed using a standard MIT (thiazolyl blue tetrazolium bromide) assay, i.e., by adding a MTT solution to the cells, and the mixture was incubated for about 3-4 hours at about 37° C., 5% $CO_2$, after which time the amount of formazan produced by the NHEK cells from cellular metabolism of MTT was measured by reading the optical density (OD) at 560 nm and subtracting background at 670 nm. The average OD so measured from the six samples of each treatment is directly indicative of the relative viability of the respective NHEK cell cultures after such treatment.

Figure 3:
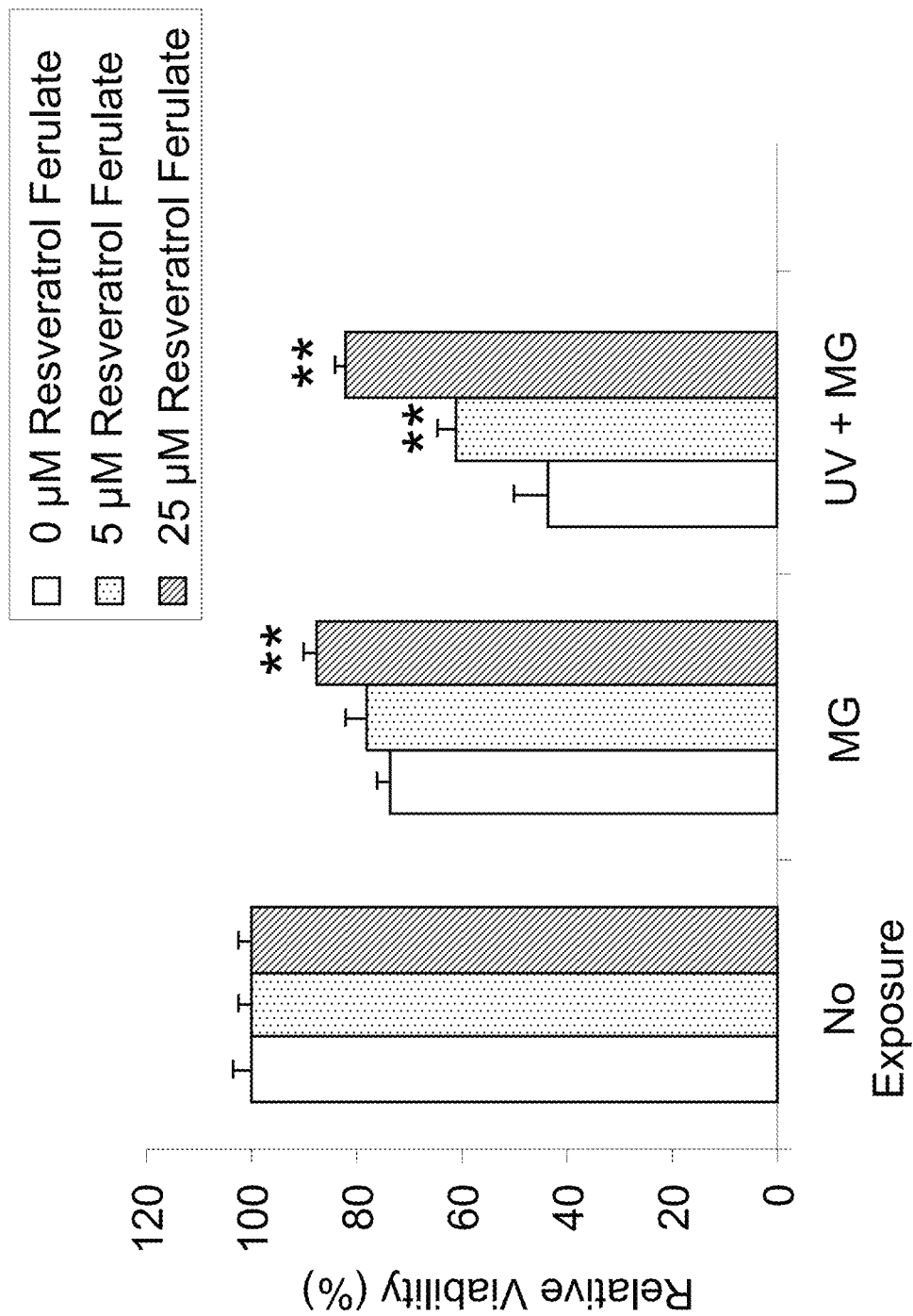
FIG. 3 is a chart showing the relative cell viability of NHEK cell cultures treated with resveratrol ferulates at various concentrations before and after exposure to either methylglyoxal (MG) alone or methylglyoxal in combination with UV light (UV+MG).
Figure 4:
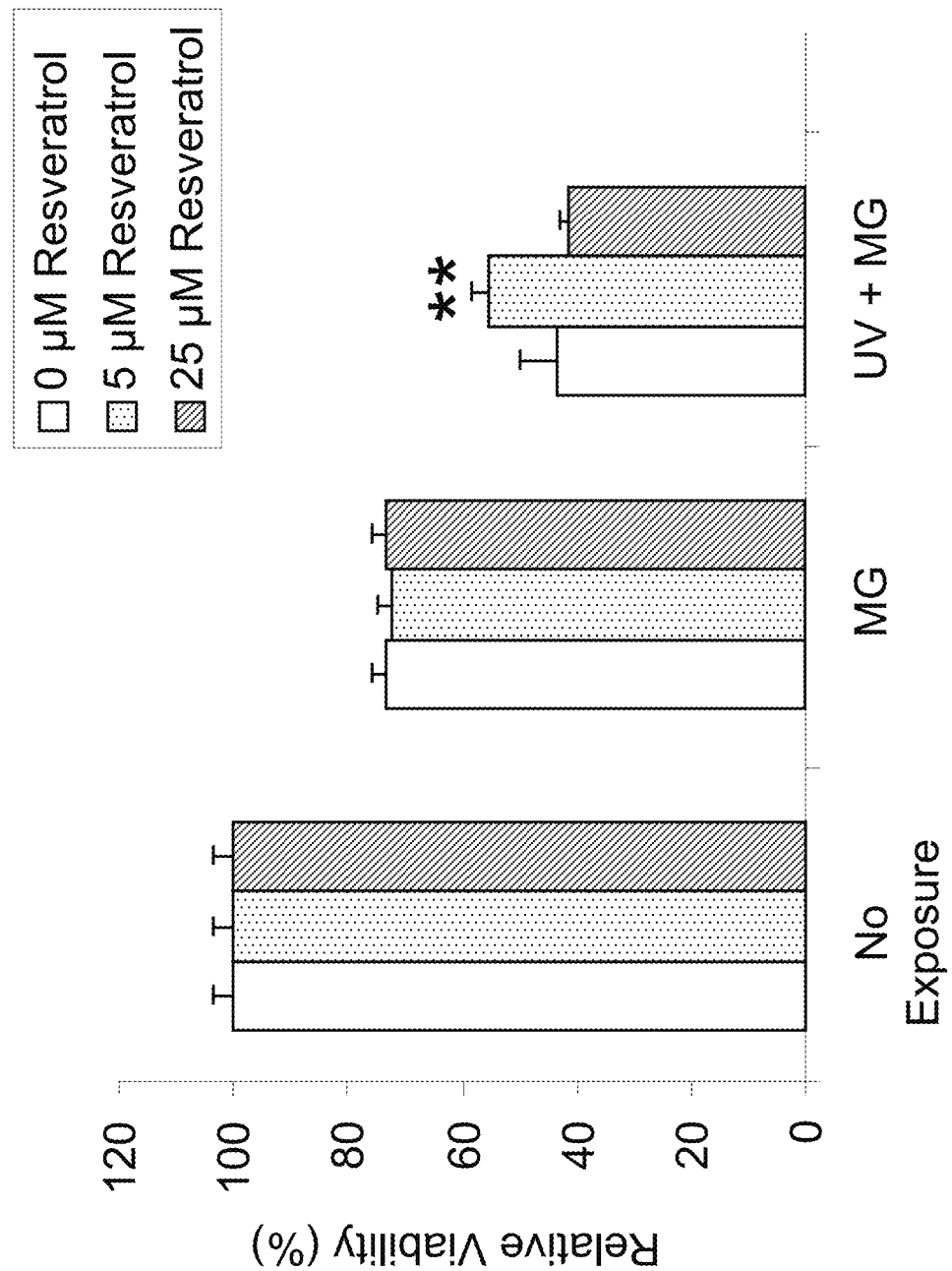
FIG. 4 is a chart showing the relative cell viability of NHEK cell cultures treated with resveratrol at various concentrations before and after exposure to either methylglyoxal (MG) alone or methylglyoxal in combination with UV light (UV+MG).
Figure 5:
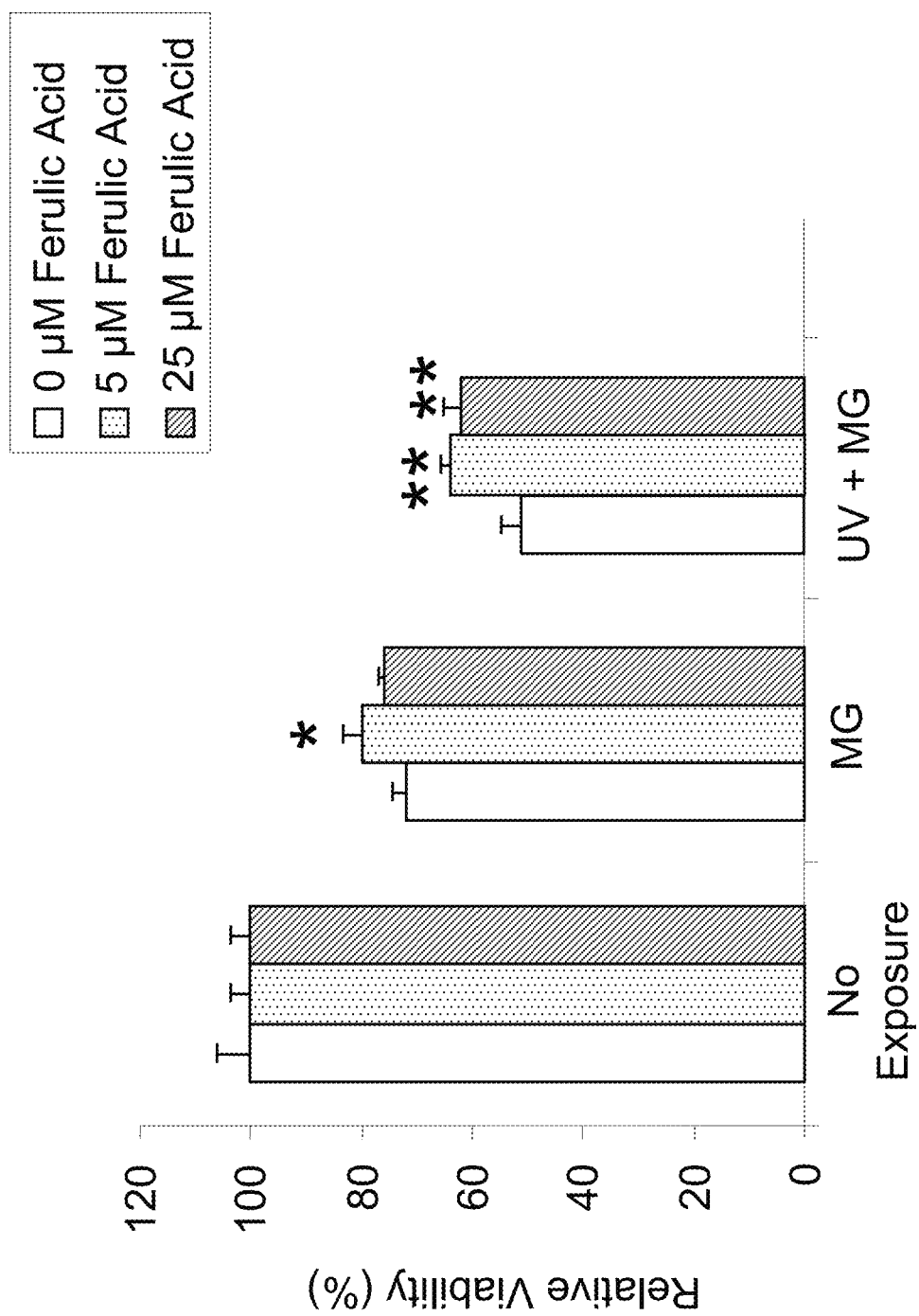
FIG. 5 is a chart showing the relative cell viability of NHEK cell cultures treated with ferulic acid at various concentrations before and after exposure to either methylglyoxal (MG) alone or methylglyoxal in combination with UV light (UV+MG).

FIG. 3 shows the relative viability of the NHEK cells treated with resveratrol ferulates at concentrations of 0.5, and 25 µM as measured before and after exposure to either MG alone or combination of MG and UV. FIG. 4 shows the relative viability of the NHEK cells treated with resveratrol at concentrations of 0.5, and 25 µM as measured before and after exposure to either MG alone or combination of MG and UV. FIG. 5 shows the relative viability of the NHEK cells treated with ferulic acid at concentrations of 0.5, and 25 µM as measured before and after exposure to either MG alone or combination of MG and UV. The viability of NHEK cells measured before exposure to MG or combination of MG and UV was arbitrarily set as 100% for all treatments.

A percentage protection (%) value was calculated for each treatment based on the relative viability shown in FIGS. 3-5, as follows:

$$\frac{RV_{T/E} - RV_{U/E}}{RV_{U/N} - RV_{U/E}} \times 100\%$$

wherein $RV_{U/N}$ is the relative viability of un-treated, non-exposed NHEK cells (i.e., the respective active concentration was 0 µM, and the viability was measured before exposure to either MG or combination of MG and UV), $RV_{U/E}$ is the relative viability of the un-treated, exposed NHEK cells (i.e., the respective active concentration was 0 µM, and the viability was measured after exposure to either MG or combination of MG and UV), and $RV_{T/E}$ is the relative viability of the treated, exposed NHEK cells (i.e., the cells were treated with the respective active, i.e., resveratrol ferulates, resveratrol, or ferulic acid, at 5 or 25 µM, and the viability was measured after exposure to either MG or combination of MG and UV). The resulting data were analyzed by Factorial Analysis of Variance (ANOVA), and if effects within factors were deemed significant, Tukey HSD (Honestly Significantly Different) post-hoc tests were then used to identify which group differed from others. The single asterisk (*) in FIGS. 3-5 represents p<0.05 (i.e., significant), and the double asterisk (**) in FIGS. 3-5 represents p<0.01 (i.e., highly significant).

Resveratrol ferulates demonstrated a percentage protection value of about 18% at the treatment concentration of 5 µM and about 53% at the treatment concentration of 25 µM when the NHEK cells were exposed to MG alone. When the NHEK cells were exposed to the combination of MG and UV, resveratrol ferulates demonstrated a percentage protection value of about 31% at the treatment concentration of 5 µM and about 68% at the treatment concentration of 25 µM. In contrast, the percentage protection values associated with resveratrol and ferulic acid of 5 and 25 µM were all below 25% when the NHEK cells were exposed to either MG alone or the combination of MG and UV, indicating that resveratrol ferulates provided significantly stronger protection against either MG alone or the combination of MG and UV than resveratrol or ferulic acid.

EXAMPLE 5

Cosmetic or Skin Care Compositions Containing Resveratrol Ferulate

Formulas 1 & 2

Skin treatment oil-in-water (1), and oil-in-water-in-silicone oil (2), creams were prepared as follows:

| Ingredient | w/w % | |
|---|---|---|
| | 1 | 2 |
| Water | QS | QS |
| Hydroxyethyl urea | 0.50 | |
| Hyaluronic acid | 9.00 | 9.00 |
| Disodium EDTA | 0.12 | |
| Creatine | 0.05 | |
| Sucrose | 0.50 | |
| Caffeine | 0.20 | |
| Caprylyl glycol | 0.40 | 0.28 |
| Caprylic/capric triglyceride/cetyl alcohol/C12-20 acid PEG-8 ester | 4.00 | |
| PEG-100 stearate | 1.20 | |
| C12-20 acid PEG-8 ester | 4.96 | |
| Caprylic/capric triglyceride | 0.55 | |
| Behenyl alcohol | 0.50 | |

-continued

| Ingredient | w/w % | |
|---|---|---|
| | 1 | 2 |
| Coco caprylate caprate | 5.10 | |
| Sweet almond oil | 0.10 | |
| Dimethicone, 100 cst. | 2.50 | |
| Dimethicone, 6 cst | | 5.00 |
| Dimethicone (silicone gum/20 cst dimethicone blend) | | 8.00 |
| Dimethicone/polysilicone 11 | | 6.00 |
| Dimethicone/dimethicone PEG-10/15 crosspolymer | | 1.00 |
| Lauryl PEG-9 polydimethylsiloxyethyl dimethicone | | 1.00 |
| Sesame oil | 0.10 | |
| Potassium cetyl phosphate | 0.50 | |
| Apricot kernel oil | 0.10 | |
| Wheat bran extract/olive extract | 0.20 | 0.20 |
| Cholesterol | 0.20 | |
| Linoleic acid | 0.20 | |
| Cholesterol/potassium sulfate | 0.20 | |
| Theobroma grandiflorum seed butter | 1.40 | |
| Lauryl PCA | 0.01 | 1.00 |
| Dimethicone | 1.50 | |
| Phenoxyethanol | 0.70 | 0.60 |
| Water/polyaminopropyl biguanide | 0.40 | |
| Glycerin | 2.00 | |
| Butylene glycol | 1.00 | |
| Hexylene glycol | | 0.05 |
| Mica/titanium dioxide | 1.00 | 0.75 |
| Mica/titanium dioxide/triethoxycaprylyl silane | | 0.50 |
| Pearl powder | 0.001 | |
| Silica | 0.50 | |
| 30% aqueous sodium hydroxide | 0.35 | |
| Trehalose | 0.50 | |
| N-acetyl glucosamine | 1.00 | 1.00 |
| Water/purified aribodopsis thaliana extract/lecithin | 0.50 | 1.00 |
| Aqueous solution acetyl hexapeptide-8 | 1.00 | 1.00 |
| Yeast ferment extract | 1.00 | 1.00 |
| Water/lecithin/micrococcus lysate | 0.50 | 0.50 |
| Milk protein/lactose/glucose/fructose | 0.50 | 0.50 |
| Saccharide isomerate | 0.50 | |
| Whey protein | 0.50 | 0.56 |
| Water/butylene glycol/lecithin/lauryldimonium hydroxypropyl hydrolyzed soy protein/lecithin/xanthan gum/ascorbyl tocopheryl maleate | 1.00 | 1.00 |
| Glycerin/padina povonica extract | 0.10 | 0.10 |
| Thermus thermophillus ferment/glycerin | 0.05 | |
| Camelina sativa seed oil | 0.05 | |
| Water/gold/hydrolyzed wheat protein | 0.001 | |
| Sorbitol/water/ascophyllum nodosum extract/asparagopsis armata extract | 0.25 | |
| Butylene glycol | 0.50 | |
| Resveratrol Ferulates | 0.50 | 0.50 |
| Boswellia serrata extract | 0.05 | |
| Calophyllum inophyllum (tamanu) seed oil | 0.05 | |
| Fragrance | 0.20 | |
| FD&C yellow No. 5 (1% aqueous solution) | 0.05 | |
| Aminomethyl propanol | | 0.03 |
| Sodim phosphate dibasic (10% aqueous solution) | | 0.75 |
| Citric acid (10% aqueous solution) | | 0.008 |
| Sodium acrylate/sodium acryloyldimethyl taurate copolymer/hydrogenated polydecene/laureth-8 | 1.00 | 1.00 |
| Ammonium acrylodimethyltaurate/VP copolymer | 0.70 | |
| Water/butylene glycol/decarboxy carnosine HCl | | 0.50 |

The composition was prepared by combining the water phase and oil phase ingredients separately, then emulsifying to form an emulsion.

Formula 3

A water-in-silicone oil emulsion skin serum was prepared as follows:

| Ingredient | w/w % |
|---|---|
| Dimethicone/dimethicone PEG-10/15 crosspolymer | 4.00 |
| Dimethicone/dimethiconol | 1.00 |
| Dimethicone, 6 cst. | 6.00 |
| Trisiloxane (1.0 cst) | 16.00 |
| Water | QS |
| Phenoxyethanol | 0.50 |
| Caprylyl glycol/phenoxyethanol/hexylene glycol/iodopropynyl butylcarbamate | 0.50 |
| Water/polyaminobiguanide | 0.20 |
| Butylene glycol | 2.00 |
| Resveratrol Ferulates | 0.50 |
| Glycerin | 10.00 |
| Ammonium acrylodimethyltaurate/VP copolymer | 0.50 |
| Sodium citrate | 0.50 |

The composition was prepared by combining the oil phase ingredients and water phase ingredients separately, then mixing well to emulsify.

Formula 4

Emulsion foundation makeup compositions were prepared as follows:

| Ingredient | w/w % |
|---|---|
| Cyclomethicone | 16.90 |
| Polysilicone-11 | 5.00 |
| Cyclomethicone/dimethiconol | 1.00 |
| Dimethicone copolyol | 1.50 |
| Sorbitan sesquioleate | 1.50 |
| Phenyl trimethicone | 10.00 |
| Dimethicone | 10.00 |
| Red Iron Oxide treated with methicone | 0.50 |
| Yellow iron oxide treated with methicone | 1.22 |
| Black iron oxide treated with methicone | 0.13 |
| Titanium dioxide coated with methicone | 8.06 |
| Water | QS |
| Butylene glycol | 5.00 |
| Resveratrol Ferulates | 0.50 |
| Xanthan gum | 0.10 |
| Magnesium sulfate | 1.00 |
| Laureth-7 | 0.25 |

The water, oil and pigment phases were separately prepared by low shear mixing. The phases were combined with high shear blending to form a foundation makeup composition.

Formula 5

A water-in-oil skin treatment composition was prepared as follows:

| Phase | Ingredients | w/w % |
|---|---|---|
| 1 | Peg-30 dipolyhydroxystearate | 1.125 |
| 1 | Polyglyceryl-2-trisostearate | 0.400 |
| 1 | Isostearic acid | 1.000 |
| 1 | PPG-15 stearylether | 4.000 |
| 1 | Trimethylolpropane triisostearate | 2.000 |
| 1 | Stearic acid | 0.200 |
| 1 | Palmitic acid | 0.300 |
| 1 | Hydrogenated lecithin | 3.000 |
| 1 | Soybean sterol | 1.000 |
| 1 | Squalane | 2.500 |
| 2 | De-ionized water | 75.575 |
| 2 | Arginine | 0.200 |
| 3 | Glycerin | 5.000 |
| 3 | Resveratrol Ferulates | 1.000 |

-continued

| Phase | Ingredients | w/w % |
|---|---|---|
| 4 | Caprylylglycol/phenoxyethanol/hexyleneglycol | 0.700 |
| 5 | Hyaluronic acid (1% sol) | 2.000 |

Heat the oil phase and water phase at 80° C. and the slowly add the water phase into the oil phase, mix well, cool down to 40° C. and then add phase 3, 4, and 5.

Formula 6

An oil-based, anhydrous skin treatment composition was prepared as follows:

| Phase | Ingredients | w/w % |
|---|---|---|
| 1 | Ozokerite wax | 3.5 |
| 1 | Cetyl esters | 3.5 |
| 1 | Beeswax | 3.5 |
| 1 | Petrolatum | 16.5 |
| 1 | Glyceryl dilaurate | 15.0 |
| 1 | Glyceryl stearate&Behenyl alcohol&palmitic acid&stearic acid&lecithin&lauryl alcohol&myristil alcohol &cetyl alcohol | 4.0 |
| 1 | Shea butter | 15.0 |
| 1 | Ethylhexyl palmitate | 8.0 |
| 1 | Myristyl myristate and Myristyl laurate | 10.0 |
| 1 | Isodecylneopentanoate | 18.7 |
| 2 | Isopropylparaben &isobutylparaben &butylparaben | 0.6 |
| 2 | Tocopheryl acetate | 0.1 |
| 2 | Fragrance | 0.1 |
| 2 | Butylene glycol | 1.0 |
| 2 | Resveratrol Ferulates | 0.5 |

Combine all ingredients in Phase 1 and heat to 80° C. until clear with stirring, cool to 55° C. and add phase 2, mix well, pour at 50° C. in a proper container.

Formula 7

An oil-and-silicone based, anhydrous skin treatment composition was prepared as follows:

| Phase | Ingredients | w/w % |
|---|---|---|
| 1 | Glyceryl behenate | 14.0 |
| 1 | Macadamia nut oil | 20.0 |
| 1 | Cyclomethicone | 57.8 |
| 1 | Dimethicone | 5.0 |
| 2 | Maltodextrin and papaya extract | 1.0 |
| 2 | Butylene glycol | 1.0 |
| 2 | Resveratrol Ferulates | 0.5 |
| 2 | Tocopheryl acetate | 0.5 |
| 2 | Fragrance | 0.2 |

Heat Phase 1 at 75° C., cool down while stirring, at 30° C. add Phase 2. While completing the cooling, homogenize the mixture.

Formula 8

A silicone-based, anhydrous skin treatment composition was prepared as follows:

| Phase | Ingredients | w/w % |
|---|---|---|
| 1 | Dimethicone/vinyldimethicone crosspolymer/methyltrimethicone | 76.1 |
| 1 | Cyclomethicone/dimethicone/C30-40 olefin/phenylmethicone/stearoxytrimethylsilane | 2.7 |
| 1 | Methyl Trimethicone | 9.0 |
| 1 | PEG10 Dimethicone | 1.0 |
| 2 | Butylene glycol | 10.0 |
| 2 | Phenoxyethanol | 0.2 |
| 3 | Resveratrol Ferulates | 1.0 |

Mix well phase 1 at room temperature, homogenize if needed, and then add phase 2 and 3 while mixing.

Formula 9

A silicone-in-water skin treatment composition was prepared as follows:

| Phase | Ingredients | w/w % |
|---|---|---|
| 1 | De-ionized water | 67.610 |
| 1 | Disodium EDTA | 0.020 |
| 1 | Chlorophenesin | 0.100 |
| 2 | Polysorbate 40 | 2.556 |
| 3 | Dimethicone | 5.000 |
| 3 | Cyclopentasiloxane | 15.000 |
| 3 | Myristyl alcohol | 2.000 |
| 4 | Pentylene glycol | 2.000 |
| 4 | Resveratrol Ferulates | 0.500 |
| 4 | Phenoxyethanol | 0.790 |
| 4 | Polysorbate 40 | 0.200 |
| 5 | Polyacrylamide/$C_{13}$-$C_{14}$ isoparaffin/laureth-7 | 3.670 |
| 5 | Polysorbate 40 | 0.550 |

The components of Phase 1 were added into a main kettle and mixed with a Greerco mixer at about 65° C. until all the solids were dissolved and the mixture became clear. Phase 2 components were then added into the main kettle and mixed with the Greerco mixer at 65° C. until the mixture became clear. In a support kettle, the components of Phase 3 were added and mixed with a propeller mixer at 65° C. until a clear mixture was formed, which was then added to the main kettle and continued to be mixed with the Greerco mixer at 65° C. to form a homogeneous mixture. In an auxiliary kettle, the components of Phase 4 were mixed together first with a propeller mixer at 60° C. and then with a Silverson mixer until a homogeneous mixture was formed, which was then added to the batch in the main kettle and continued to be mixed with the Greerco mixer. The resulting mixture was cooled to 30° C. Mixing was continued after replacing a side-wipe until a homogeneous mixture was formed. Phase 5 components were added to the mixture and continued to be mixed with a side-wipe until a homogeneous mixture was obtained.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What is claimed is:
1. A method for lightening skin and/or reducing reactive oxygen species in skin in need of thereof comprising applying to said skin a cosmetic composition comprising an ester of resveratrol consisting of a mixture of 3-ferulate-5,4'-dihydroxystilbene; 4'-ferulate-3,5-dihydroxystilbene; 3,5-diferulate-4'-hydroxystilbene; 3,4'-diferulate-5-hydroxystilbene; 3,5,4'-triferulate-hydroxystilbene.

2. The method of claim 1 for lightening skin wherein the cosmetic composition is applied to selected areas of skin with hyperpigmentation to reduce hyperpigmentation in such selected areas.

3. The method of claim 1, wherein the cosmetic composition is applied to facial skin to achieve skin lightening and/or reducing reaction oxygen species thereon.

4. The method of claim 1, wherein the mixture is present in the cosmetic composition in an amount ranging from about 0.001% to about 20% by total weight of the composition.

5. The method of claim 4, wherein the mixture is encapsulated by one or more vesicles, microspheres, nanospheres, capsules, or mixtures thereof.

6. The method of claim 1, wherein the topically or cosmetically acceptable carrier is an emulsion comprising an aqueous phase and an oil phase.

7. The method of claim 6, wherein the mixture is dispersed or solubilized in the aqueous phase of the emulsion.

8. The method of claim 6, wherein the mixture is dispersed or solubilized in the oil phase of the emulsion.

9. The method of claim 1, wherein the cosmetic composition is anhydrous.

* * * * *